United States Patent
Neshat

(10) Patent No.: US 11,992,482 B2
(45) Date of Patent: May 28, 2024

(54) MALLEABLE CONTROLLED RELEASE LOCAL ANESTHETIC WITH HEMOSTATIC COMPOSITION

(71) Applicant: Rilento Pharma, LLC, Raleigh, NC (US)

(72) Inventor: Khashayar Kevin Neshat, Raleigh, NC (US)

(73) Assignee: Rilento Pharma, LLC, Raleigh, NC (US)

(*) Notice: Subject to any disclaimer, the term of this patent is extended or adjusted under 35 U.S.C. 154(b) by 0 days.

(21) Appl. No.: 15/405,453

(22) Filed: Jan. 13, 2017

(65) Prior Publication Data

US 2018/0169080 A1    Jun. 21, 2018

Related U.S. Application Data

(60) Provisional application No. 62/437,193, filed on Dec. 21, 2016.

(51) Int. Cl.
| | |
|---|---|
| *A61K 31/445* | (2006.01) |
| *A61K 9/06* | (2006.01) |
| *A61K 9/16* | (2006.01) |
| *A61K 9/19* | (2006.01) |
| *A61K 38/48* | (2006.01) |
| *A61K 45/06* | (2006.01) |
| *A61L 24/00* | (2006.01) |
| *A61P 23/02* | (2006.01) |

(52) U.S. Cl.
CPC ............ *A61K 31/445* (2013.01); *A61K 9/06* (2013.01); *A61K 9/1647* (2013.01); *A61K 9/19* (2013.01); *A61K 38/4833* (2013.01); *A61K 45/06* (2013.01); *A61L 24/0015* (2013.01); *A61L 24/0036* (2013.01); *A61L 24/0094* (2013.01); *A61P 23/02* (2018.01); *C12Y 304/21005* (2013.01); *A61L 2300/402* (2013.01); *A61L 2300/404* (2013.01); *A61L 2300/418* (2013.01)

(58) Field of Classification Search
None
See application file for complete search history.

(56) References Cited

U.S. PATENT DOCUMENTS

| | | | |
|---|---|---|---|
| 3,029,188 A | 4/1962 | Cyr et al. | |
| 3,157,524 A | 11/1964 | Artandi | |
| 4,293,539 A | 10/1981 | Ludwig | |
| 4,600,533 A * | 7/1986 | Chu | A61L 26/008 |
| | | | 128/DIG. 8 |
| 4,622,219 A | 11/1986 | Haynes | |
| 4,725,442 A | 2/1988 | Haynes | |
| 4,938,763 A | 7/1990 | Dunn et al. | |
| 5,061,492 A | 10/1991 | Okada et al. | |
| 5,188,837 A | 2/1993 | Domb | |
| 5,922,340 A | 7/1999 | Berde | |
| 6,217,911 B1 * | 4/2001 | Vaugn | A61K 9/5026 |
| | | | 424/422 |
| 6,261,582 B1 | 7/2001 | Needham et al. | |
| 8,481,074 B2 | 7/2013 | Shalaby et al. | |
| 8,523,569 B2 * | 9/2013 | Neshat | A61K 9/0024 |
| | | | 424/422 |
| 2005/0123588 A1 * | 6/2005 | Zhu | A61L 26/0052 |
| | | | 424/443 |
| 2007/0110804 A1 | 5/2007 | Royer | |
| 2008/0241245 A1 | 10/2008 | Myers et al. | |
| 2009/0192429 A1 | 7/2009 | Daniels et al. | |
| 2009/0202642 A1 * | 8/2009 | Huang | A61K 9/0024 |
| | | | 424/488 |
| 2009/0264472 A1 * | 10/2009 | Wohabrebbi | A61K 9/0024 |
| | | | 514/330 |
| 2011/0301131 A1 | 12/2011 | Fitzpatrick | |
| 2013/0108671 A1 * | 5/2013 | McCoy | A61M 5/19 |
| | | | 424/400 |
| 2015/0283286 A1 | 10/2015 | Eastwood et al. | |
| 2020/0069595 A1 | 3/2020 | Neshat | |

FOREIGN PATENT DOCUMENTS

| | | |
|---|---|---|
| WO | 9405265 | 3/1994 |
| WO | 9405265 A1 | 3/1994 |

OTHER PUBLICATIONS

Krill, David et al. Topical Thrombin and Powdered Gelfoam: An Efficient Hemostatic Treatment for Surgery. Journal of Tenn Dent Assoc. 66(2): pp. 26-27. (Year: 1986).*
Neshat, Kevin; Non-Final Office Action for U.S. Appl. No. 16/555,669, filed Aug. 29, 20219, dated Aug. 2, 2021, 43 pgs.
Neshat, Kevin; Final Office Action for U.S. Appl. No. 16/555,669, filed Aug. 29, 20219, dated May 26, 2022, 28 pgs.
Neshat, Kevin; Advisory Action for U.S. Appl. No. 16/555,669, filed Aug. 29, 2019, dated Nov. 3, 2022, 3 pgs.
Neshat, Kevin; Non-Final Office Action for U.S. Appl. No. 16/555,669, filed Aug. 29, 20219, dated Mar. 16, 2023, 36 pgs.
Neshat, Kevin; Requirement for Restriction/Election for U.S. Appl. No. 16/555,669, filed Aug. 29, 2019, dated Dec. 10, 2020, 9 pgs.
Neshat, Kevin; Final Office Action for U.S. Appl. No. 16/555,669, filed Aug. 29, 20219, mailed Feb. 1, 2024, 14 pgs.

* cited by examiner

*Primary Examiner* — Nghi V Nguyen
(74) *Attorney, Agent, or Firm* — Taylor English Duma LLP

(57) ABSTRACT

A malleable sustained release formulation is created utilizing a local anesthetic wherein the composition is made sustained release by incorporating it into a bovine or porcine hemostatic agent. The composition is malleable enough to fit into a cavity such as a dental cavity and form the shape of the cavity. In addition to providing sustained release of the anesthetic, the composition also provides quicker reduction in bleeding.

13 Claims, No Drawings

MALLEABLE CONTROLLED RELEASE LOCAL ANESTHETIC WITH HEMOSTATIC COMPOSITION

This application claims priority to a provisional application No. 62/437,193 filed on Dec. 21, 2016, which is incorporated herein in its entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

Field of the Invention

The present invention relates to novel compositions for treating post-operative pain. In particular, the present invention provides novel pharmaceutical formulations for delivery of local anesthetics and a hemostatic composition for post-operative pain, for implantation into a dental extraction, wound or surgical cavity.

Description of Related Art

Local anesthetics are designed to block the conduction and generation of the sense of pain by increasing the perceived threshold for excitation in the corresponding nerve that transmits the sensation. It accomplishes this by slowing down the propagation of an impulse through the nerve and by reducing the rate of rise of the action potential of the nerve. Local anesthetics are considered very potent and their use usually results in complete loss of the sensation of feeling in the area to which a local anesthetic is administered. The sensations that local anesthetics block include pain, temperatures sensation, touch, proprioception, and skeletal muscle tone.

Some of the commonly used local anesthetics include mepivicaine, xylocaine and bupivicaine. These local anesthetics are of medium duration with half-lives somewhere in the about 2 to 3 hour range with effects lasting out to as long as about 20 hours. Frequently the local anesthetics are mixed with epinephrine, a potent vasoconstrictor. Epinephrine reduces the clearance of the local anesthetic thus extending the effective time of action even further. This action is ideal for dental type surgery, for example, during tooth extraction. Local anesthetics are preferred over general anesthetics in localized dental surgery because of the complications that can occur with general anesthesia. Even when general anesthetics are used in dental surgery, a local anesthetic is still used along with the general anesthetic to insure a reduction in pain as the general anesthetic wears off.

The local anesthetics are designed to remain active during dental or other surgery or conditions and beyond that for pain moderation. Severe pain from dental extraction, wounds and other surgery in most people lasts somewhere around 1 to 5 days after dental surgery and typically a centrally acting narcotic is given such as meperidine, oxycodone, hydrocodone, or codeine to mitigate pain during this time period. The opiate drugs act through the opiate receptors in the central nervous system and are usually orally self-medicated after dental surgery. It is also typical that a prescription is given for these opiate medications and by the time the patient fills the prescription, takes the oral medication and it begins to work, the local anesthetic has begun to wear off sufficiently that there is not an adverse additive effect. Although centrally acting narcotics are very effective in the treatment of post-surgical dental pain, they are associated with serious side effects, including nausea and vomiting, addiction, respiratory depression, apnea, circulatory depression, respiratory arrest, shock and cardiac arrest.

Post dental surgery administration of additional local anesthetics would be preferable. However, the ability to administer additional local anesthetics is beyond the skills of the average patient. Furthermore, the additive effects of overlapping dosages if anesthetic administration is not timed properly can create risks that make patient self-dosing unacceptable. Even further, since access to the socket cavity is achieved right after tooth extraction before the initial local anesthetic has begun to wear off, timing the administration in the socket at that time during the procedure with current products can also lead to a dangerous additive effect.

The administration of local anesthetics with a long duration has been used to reduce the number of times a local anesthetic needs to be administered. A number of different approaches have been attempted to extend the life of the local anesthetics. Approaches have included the addition of epinephrine added to the local anesthetic mentioned above as well as long acting or sustained released injectable formulations of a local anesthetic. While these products could be dosed after surgery as well, they do not take into consideration the pre-surgical doses and their rapid onset creates a substantial risk of overdose. Sustained release carriers for injectable local anesthetics have been described. For example, U.S. Pat. Nos. 4,725,442 and 4,622,219 (Haynes) are directed to methoxyflurane-containing microdroplets coated with a phospholipid prepared by sonication, which are suitable for intradermal or intravenous injection into a patient for inducing local anesthesia. Such microdroplets are said to cause long-term local anesthesia when injected intradermally, giving a duration of anesthesia considerably longer than the longest acting conventional local anesthetic (bupivacaine).

U.S. Pat. No. 5,188,837 (Domb) relates to a microsuspension system containing lipospheres having a layer of a phospholipid imbedded on their surface. The core of the liposphere is a solid substance to be delivered, or the substance to be delivered is dispersed in an inert vehicle. The substance to be delivered can be, e.g., nonsteroidal anti-inflammatory compounds, local anesthetics, water insoluble chemotherapeutic agents and steroids.

Other formulations directed to injectable microcapsules, etc. are known. For example, U.S. Pat. No. 5,061,492 (Okada et al.) describes prolonged release microcapsules of a water-soluble drug in a biodegradable polymer matrix which is composed of a copolymer of glycolic acid and a lactic acid. The microcapsules are prepared as an injectable preparation in a pharmaceutically acceptable vehicle. The particles of water soluble drug are retained in a drug-retaining substance dispersed in a matrix of the lactic/glycolic acid copolymer in a ratio of 100/1 to 50/50 and an average molecular weight of 5,000-200,000. The injectable preparation is made by preparing a water-in-oil emulsion of an aqueous layer of drug and drug retaining substance and an oil layer of the polymer, thickening and then water-drying.

U.S. Pat. No. 4,938,763 (Dunn, et al.) is related to a biodegradable polymer for use in providing syringe able, in-situ forming, solid biodegradable implants for animals. In one aspect of this reference, a thermosetting system is utilized which utilizes copolymers which may be derived from polylactides and/or polyglycolides, combinations and mixtures of these and other polymers.

U.S. Pat. No. 4,293,539 (Ludwig, et al.) is directed to controlled release formulations comprised of a microbial agent dispersed throughout a copolymer derived from lactic acid and glycolic acid. The copolymer is derived from 60-95% lactic acid and 40-50% glycolic acid by weight, and has a molecular weight of 6,000-35,000. An effective amount of the copolymeric formulation is administered by subcutaneous or intramuscular administration.

PCT publication WO1994/005265 (Berde et al.) describes improved biodegradable sustained release systems consisting of a polymeric matrix incorporating a local anesthetic for the prolonged administration of the local anesthetic agent. The devices are selected on the basis of their degradation profiles: release of the topical anesthetic in a linear, controlled manner over the period of preferably two weeks and degradation in vivo with a half-life of less than six months, more preferably two weeks, to avoid localized inflammation. Tile disclosure states that all anti-inflammatory can be incorporated into the polymer with the local anesthetic to reduce encapsulation for optimal access of drug to its site of action. The anti-inflammatories that are said to be useful include steroids such as dexamethasone, cortisone, prednisone, and others routinely administered orally or by injection.

U.S. Pat. No. 8,523,569 (Neshat) describes methods of delivering a local anesthetic such as bupivacaine to a tooth socket for timed release activity of a local anesthetic. In addition, the addition of certain augmentation agents are described as included in the formulation as well as a number of sustained release materials. The formulations are designed to release between about 4 hours and 5 days.

It would, accordingly, be useful to have a composition and method that allows the use of local anesthetics in dental surgery, especially tooth extraction, for placement in the open socket in addition to a hemostatic composition, especially if the hemostatic composition could also act as the sustained release media.

BRIEF SUMMARY OF THE INVENTION

The present invention relates to the surprising discovery that a formulation of a local anesthetic for use in a dental extraction cavity can be formulated with an absorbable hemostatic composition to produce a sustained release of local anesthetic for up to several days in a dental extraction, wound or surgical cavity with hemostatic properties and in one embodiment, without use of other thickening agents. It is surprisingly found that use of the material increases activity of the patient.

Accordingly, in one embodiment, there is a malleable sustained release formulation of a local anesthetic and a hemostatic composition designed for packing in a dental extraction, surgical or wound cavity of a patient comprising:
  a) a local anesthetic;
  b) an absorbable hemostatic composition; and
  c) wherein the anesthetic and the hemostatic composition are combined to form a sustained release of the local anesthetic which is malleable such that it is or can be sized and shaped to fit the cavity.

DETAILED DESCRIPTION OF THE INVENTION

While this invention is susceptible to embodiment in many different forms, and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings, if any. This detailed description defines the meaning of the terms used herein and specifically describes embodiments in order for those skilled in the art to practice the invention.

Definitions

The terms "about" and "essentially" mean±10 percent.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

The term "comprising" is not intended to limit inventions to only claiming the present invention with such comprising language. Any invention using the term comprising could be separated into one or more claims using "consisting" or "consisting of" claim language and is so intended.

Reference throughout this document to "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings, if any, featured in the figures, if any, are for the purpose of illustrating certain convenient embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein, dental "local anesthetics" refers to those local anesthetics which can be used during oral/dental surgery for the extraction of teeth. Typically, they are injected but in the present invention they are reformulated for sustained release and work in a topical manner. Local anesthetics include bupivacaine, mepivicaine, articaine, ropivacaine, dibucaine, etidocaine, tetracaine, lidocaine, xylocaine, and the like including mixtures and/or salts and/or derivatives thereof. These local anesthetics have a variable half-life and duration and are selected based on their various properties and compatibility with the particular patient and second anesthetic matched with the properties of the first local anesthetic. They are formulated into a sustained release formulation with hemostatic properties as described elsewhere herein. In one embodiment, the local anesthetic is formulated into microparticles utilizing poly (lactic-co-glycolic acid) (PLGA) before being formulated with a hemostatic composition. Microparticles are particles generally between about 0.1 and 100 micrometers. Dosage of the local anesthetic will depend on the anesthetic chosen, the degree of pain and surgical conditions and can be determined based on disclosures herein. In one example, Bipuvicaine preparations can be given. Such release gives between about 0.1 to about 5 mg/kg/day. In other embodiment, the dose is 0.25, 0.5 or 1 mg/kg/day. Loading of the anesthetic will depend on the composition selected and the dosage required and the size of the extraction cavity and the like. In general, from about 0.1% to about 40% anesthetic on a wt/wt basis of the total composition can be utilized. Where a hemostatic composition is utilized, no further viscosity agents are needed to achieve sustained release.

For example, a relatively long-acting local anesthetic bupivacaine hydrochloride is commercially available as Marcaine™ hydrochloride in sterile isotonic solutions with and without epinephrine (as bitartrate) 1:200,000 for injection via local infiltration, peripheral nerve block, and caudal and lumbar epidural blocks. This local anesthetic could be formulated into the formulation of the present invention such that it is dosed as suggested above.

The surgical removal of a tooth, i.e. tooth extraction, to produce an extraction cavity is normally accomplished by prior administration of local anesthetics often accompanied with general anesthesia in an oral surgery case. A local anesthetic or mixture of local anesthetics with or without an augmenting agent is administered by injection as an infiltration or a nerve block for the extraction of a tooth. A combination of incisions, tissue reflections, elevation of teeth, sectioning of teeth with a drill or hand instrument, removal of surrounding alveolar bone, and pressure extraction with forceps is normally successful in removing a desired tooth. In some cases, the surgical site is left unsutured with only the inserted anesthetic/hemostatic of the present invention to close the surgical site. The formulation is malleable and thus can be used with any shape extraction cavity merely by pushing the formulation into the cavity. The surgery itself takes approximately 30-60 minutes from the time of injection of local anesthetic to the extraction cavity of a tooth. It is, at this point, in the tooth extraction cavity that the present invention would be administered, i.e. about 30 to 60 minutes after administration of the first local anesthetic but as desired by the surgeon. The present invention is not limited to dental extraction cavity and can be used for any soft tissue surgical incisions and wounds.

As used herein, the terms, "controlled release pharmaceutical formulation" and "sustained release" indicate a prolongation of the onset of release and a prolongation of the duration of release and/or duration of action of an active agent and are intended to be interchangeable, unless otherwise indicated.

Sustained release materials for achieving a controlled release include release materials such as controlled release polymer materials. Polymers could include polyanhydrides, copolymers of acid and glycolic acid, poly(lactic) acid, poly(glycolic) acid, polyesters, polyorthoesters, proteins, polysaccharides and/or combinations thereof. They are clearly not limited to these materials. The polymers can be biodegradable so that manual removal from the extraction cavity is avoided. Further, the materials must be biocompatible and compatible with local anesthetics.

Hemostatic composition as used herein is a composition for coagulation of blood and thus decreases bleeding. In one embodiment, it is an "absorbable hemostatic gel". The term "gel material" includes materials which are collagen or the like derived and have a hemostatic property; for example, those derived from bovine skin (e.g. Avitene™) and a hemostatic material derived from porcine skin gelatin (e.g. Gelfoam®). These compositions are designed to slow down or stop bleeding, have the advantage of being a gelling material, and used as the control release material. They are also absorbable into the body. Other hemostatic materials include—but are not limited to Hemostatic collagen (collaplug, collatape, helistat, etc.) which are soft, white, pliable, non-friable, coherent, sponge-like structures. They are fabricated from bovine collagen and are non-toxic and non-pyrogenic. Cellulose (surgical and ActCel™ hemostatic gauze) is resorbable oxidized cellulose material and is prepared as a sterile fabric mesh work. Other hemostatic materials include collagen based products (porcine, bevine, fish or the like) and/or supplementation with thrombin.

Further, the materials must be biocompatible, compatible with any other additions, and malleable into the extraction cavity. Accordingly, the formulation will be a malleable material, for example, gel, paste, slurry, putty or other rheological form that allows the composition to be placed and retained in the cavity. In one embodiment, the malleable material is a malleable gel. The size and shape will be such that the dentist or other technician can place the formulation inside the extraction cavity or incorporate the material in the incision and wound areas. Accordingly, in one embodiment, the formulation is malleable, and it can be shaped like clay or putty so that the bolus can be placed in the cavity and conform to the surrounding tissue without leaving a pocket. In another embodiment, the formulation is formed to fill the cavity sufficiently that surgical suturing is not needed and the bolus of local anesthetic becomes the closure means for the cavity. In this embodiment, the local anesthetic is formulated into a gel or other pliable surgically acceptable material for that purpose.

The controlled release aspect of the present invention formulation is particularly critical. Since it is possible there is already going to be a local anesthetic in the locality of the extraction cavity at the time of use of the present invention, application of additional local anesthetic could be toxic. Coordination of the onset of the anesthetic in the present invention and anesthetic with the release of any previous anesthetic may be necessary. Accordingly, one embodiment of the present formulation is that the timing of the onset or release and rate of release of the second local anesthetic is coordinated with the decline in levels of the first local anesthetic. For example, where the bolus is deposited in the extraction cavity after one hour and the first local anesthetic begins to decline after 2 hours and declines to insignificant levels over 6 hours, the present invention would be formulated to begin release after about one hour (or after a specifically designated time) after insertion and not release the full dosage, but rather taper in the dosage over the first 5 hours. Thus, after 6 hours the peak levels of anesthetic will have been reached as the first anesthetic has worn off. Accordingly, it is clear that the formulation must be made to be coordinated with a prior administered dental local anesthetic and not just formulated in a one-formulation-fits-all manner or a manner that would be consistent with the second local anesthetic being the only local anesthetic that is administered.

In another embodiment, the anesthetic of the present invention is fixed to release at a given time. For example, a product that releases over about 12 hours to several days e.g. 5 or more. One skilled in the art in view of this disclosure could determine the exact best way to coordinate the onset of the present invention anesthetic in view of this disclosure. In one embodiment, the effect lasts as long as about 1 day, 2 days, 3 days, 4 days, or 5 days. In another embodiment, the second administered local anesthetic has a duration of less than about 1 day. The present invention in other embodiments begins its effect at about 1, 2, 3, 4, 5 hours or longer, as desired, when utilized after other topical anesthetics.

As used herein by the phrase "sized and shaped to fit the extraction cavity" is meant that the present invention dosages designed to fit in the open socket of the jaw after tooth extraction or in a surgical or wound cavity. This can be achieved by producing the controlled release formulation of a standard size that would fit into most tooth cavities. It could also be formulated in a number of sizes so that children, men, women and very large people would all have one that is sized to the needs of the surgeon. In one embodiment, the formulation is malleable so that the surgeon can change the shape of the formulation to fit the particular cavity or such that upon inserting the formulation into the cavity, it conforms its shape to the surrounding cavity. It can also be shaped so that it conforms completely to the cavity sufficiently to seal the cavity and lessen or eliminate the need for suturing the site after tooth removal.

The formulation of the present invention will then be designed to release local anesthetic into the cavity as well as the incision sites and thus be distributed to the surrounding area for the time periods indicated above. Where the formulation of the present invention is produced of a material that decomposes within the cavity over time, no further removal of the formulation is necessary. One skilled in the art can formulate the present invention as desired.

As used herein the term "anesthetic and hemostatic materials are combined to form a sustained release of local anesthetic" refers to forming a material, e.g. a gel, with the absorbable hemostatic material and incorporating the local anesthetic into it at the designed dosage and such that it has the appropriate size as described above. In most cases, water is added to dry material and the local anesthetic but other formulations are possible. In one embodiment, micro particles of the anesthetic are utilized to aid in mixing. Depending on the material utilized, other well known procedures for distributing the anesthetic and hemostatic material into a matrix or other type suspension can be achieved.

As used herein, the term "patient" broadly refers to any animal that is to be treated with the compositions and by the methods herein disclosed. The disclosed sustained release formulation and methods for extraction cavity administration can provide prolonged and effective administration of local anesthetics. In particular, the product and method for extraction cavity administration of extended duration local anesthetic dosage formed according to the invention can provide localized pain blockade to any animal, e.g., any vertebrate, which it is desired to anesthetize. In a preferred embodiment, the term "patient" includes humans in need of or desiring prolonged treatments, such as for treatment of pain immediately following dental surgery such as tooth extraction.

Additional pharmaceutically active agents that can be incorporated into the present invention formulation of local anesthetics for extraction site administration include, e.g., antibiotics such as sulfisoxazole, penicillin G, ampicillin, cephalosporins, amikacin, gentamicin, tetracyclines, chloramphenicol, erythromycin, clindamycin, isoniazid, rifampin, and derivatives, salts and mixtures thereof; antifungals such as amphotericin B, nystatin, ketoconazole; antivirals such as acyclovir, amantadine, chlorahexidine; and other art known anti-infective.

Augmenting agents can also be included in formulations according to the present invention. They are compositions or compounds that prolong the duration of local anesthesia and/or enhance the effectiveness of local anesthetic agents when delivered to the site of local anesthetic administration. In one embodiment, thrombin is added to the formulation.

In certain embodiments of the invention, the augmenting agent can be from one or more of the following general types or classes of agents, including glucocorticosteroid agents, alkalinizing agents, non-gulcocorticoid steroids such as, e.g., neuroactive steroids and/or steroid or nonsteroid modulators of gamma amino butyric acid ("GABA") receptors, modulators of ionic transport across cell membranes, including, e.g., modulators of membrane transport of monovalent and divalent metal ions such as, for example, blockers or enhancers of sodium, potassium and/or calcium transport across cell membranes, antipyretic agents, adrenergic receptor agonists or antagonists, such as alpha 2 receptor agonists, tubulin binding agents, including, e.g., agents that are capable of either causing formation or disruption of intracellular microtubules, osmotic polysaccharides, agonists and antagonists of potassium ATP channels, i.e., able to open or close potassium ATP channels, Na, K-ATPase inhibitors and enhancers, neurokinin antagonists, PLC (i.e., phosphatidylinositol-specific phospholipase C) inhibitors, inhibitors of leukocyte glucose metabolism and anti-convulsants. The augmenting agent can also be an analeptic, a tranquilizing agent, an ataretic, an antidepressant, an anti-seizure agent, leukotriene and prostaglandin agonists and inhibitors, phosphodiesterase agonists and inhibitors, e.g., based on cAMP, and combinations of any of the foregoing. Vasoconstrictive agents provided in controlled release form also provide for unexpected and surprising augmentation of duration and potency of local anesthetics relative to immediate release forms of vasoconstrictive agents heretofore known to the art. The aforementioned types of augmenting agents may be used alone or in any mixture or combination of each such agent to provide effective augmentation of local anesthesia where desired. In one embodiment, it is mixed with other bone graft materials for preservation of sockets post extractions.

Augmenting agents that are vasoconstrictor agents in sustained release form include, but are not limited to, catecholamines, e.g., epinephrine, norepinephrine, and dopamine as well as, e.g., metaraminol, phenylephrine, methoxamine, mephentermine, methysergide, ergotamine, ergotoxine, dihydroergotamine, sumatriptan and analogs, and alpha-1 and alpha-2 adrenergic agonists, such as, e.g., clonidine, guanfacine, guanabenz and dopa (i.e., dihyrdoxyphenylalanine), methyldopa, ephedrine, amphetamine, methamphetamine, methylphenidate, ethylnorepinephrine ritalin, pemoline and other sympathomimetic agents, including active metabolites, derivatives and mixtures of any of the foregoing.

Surprisingly, locally acting vasoconstrictive agents also provide effective augmentation of local anesthesia that is unexpectedly superior to that provided by immediate release of vasoconstrictive agents. While not wishing to be bound by any hypothesis as to how vasoconstrictive agents in sustained release form might greatly prolong local-anesthetic activity, it is believed that sustained release vasoconstrictor agents provide a controlled and nontoxic vasoconstrictor activity that reduces the rate of local anesthetic washout from the treated tissue area to prolong the presence of effective concentrations of local anesthetic in the tissue. It is known to the art that vasoconstrictors, e.g., epinephrine, prolong local anesthetic activity for, at best, about 1 hour and that if excessive amounts of epinephrine or other vasoconstrictor is administered in an attempt to further prolong local anesthesia, local circulation may be so disrupted that it causes tissue necrosis and gangrene.

EXAMPLES

Example 1-Preparation of Bipivicaine (BP) Microparticles

To enable dissolution of BP within methylene chloride for the solvent evaporation method, bupivacaine hydrochloride monohydrate (Spectrum Chemical) was converted to the soluble base form, using a previously reported alkaline precipitation and filtration procedure [20]. Briefly, 25 mL of a $NaHCO_3$ solution (2.6 grams in 50 mL of $diH_2O$) was slowly added to a solution of 5 grams of BP-HCl in 150 mL of $diH_2O$. After allowing the solution to stand for approximately 10 minutes, the Bupivacaine-base (BP-base) was extracted with dichloromethane three times (150 mL each), and dried over $MgSO_4$ per the previously mentioned procedure. Solvent was then extracted via rotary evaporation and the resultant BP-base oil product was purified by precipitation and dried. Conversion results were verified via X-Ray powder diffraction (XRD). The PLGA micro particles were prepared using an emulsion-solvent evaporation method [21]. In a typical procedure, a solution comprising (500 mg) of PLGA (Sigma, ester terminated, 50:50 ratio of lactic acid to glycolic acid, 7-17K Da), and (105 mg) of BP-base in (9 mL) of methylene chloride was added to 100 mL of Trizma-buffered aqueous solution of 0.5% PVA (6000MW, Polysciences), and subsequently homogenized at ambient temperature using a handheld homogenizer for 60 seconds. The resultant emulsion was added to an additional 200 mL of 100 mM Trizma-buffered $diH_2O$, and swirled to combine. The microparticles were introduced into an Buchi rotary evaporator at 45° C. for approximately 20 minutes ramping from 1000 mbar to 215 mbar, extracting the methylene chloride. The microparticles were spun down 2 times, removing supernatant in between, to concentrate the microparticles. Particles were subsequently resuspended and washed 2-times in saline, flash frozen, lyophilized, and stored until use at 4° C.

Example 2-Preparation of Sustained Release Formulation

For PLGA microparticle/matrix formulations, 40 mg of PLGA microparticles and 50 mg of Gelfoam® (Pfizer) were weighed into a small container and combined with 150 µL of $diH_2O$. Once combined, all PLGA microparticle/matrix formulations contained a final salt concentration of 0.9 wt % NaCl. For samples without matrix, 40 mg of PLGA microparticles were directly suspended with 1 mL of 1×PBS. In both cases, the ratio of BP-PLGA microparticles to non-BP-PLGA microparticles (40 mg total of microparticles) was varied to achieve predicted dosing of BP (Table 1).

TABLE 1

Formulations for controlled release of BP*

| Targeted Dosing (mg/kg/day) | Microparticle Ratio BP-PLGA:drug-free PLGA |
|---|---|
| 1 | 1:0 |
| 0.5 | 1:1 |
| 0.25 | 1:3 |
| 0 | 0:1 |

*Each formulation contained 40 mg microparticles + 50 mg

For all formulations that contained hemostatic gel material (e.g., Gelfoam®, Avitene™ flour (Bard Davol)), samples were mixed by hand to form a moldable bolus. Periodically, the dialysis tubing was transferred to fresh buffer preconditioned at 37° C. Samples were stored at 4° C. until ultra-high performance chromatography (UHPLC) analysis. To assess diffusion of free drug through the formulation, 1 mg of unencapsulated BP (free-BP as the BP-HCl form) was added directly to either 50 mg or 100 mg of matrix. All matrix materials (Gelfoam®, Avitene™) were provided by Nulmage Surgical & Dental Implant Center.

Example 3-Formulation for Animal Testing

All formulations, with each respective vial containing enough material for 4 animals, were supplied as a lyophilized as a complex of Gelfoam®+microparticles by Research Triangle International (RTI, NC, USA). Five separate groups of males and females, with 4 animals per group, received one of the following formulation complexes: 1) Gelfoam® vehicle (GelVeh), 2) 2 mg/ml s.c. BP followed by Gelfoam® vehicle (BP+GelVeh), 3) 2 mg/ml s.c. BP followed by Gelfoam® complex with 1 mg/ml BP (BP+GelBP1™), 4) 2 mg/ml s.c. BP followed by Gelfoam® complex with 0.5 mg/ml BP (BP+GelBP.5™), and 5) 2 mg/ml s.c. BP followed by Gelfoam® complex with 0.25 mg/ml BP (BP+GelBP.25™). All samples were stored at 4° C., and prepared immediately prior to use in 600 ul 0.9% sodium chloride. The respective complexes were gently mixed with a plastic spatula (Fisherbrand™ Disposable Polypropylene Spatulas, USA), rolled into a ball between gloved fingers, and divided into four equal parts. Each ¼ was applied to a different animal in the same group.

Example 4-Animal Testing

Male and female Sprague Dawley rats, weighing between 200 g-430 g at the start of the experiment, were bred in-house from animals originally received from Charles River, NC, USA. Rats of the same sex, and within the same treatment group, were pair housed for the duration of the study, and were maintained in a climate controlled facility under a 12-hour light/dark cycle. Rats had ad libitum access to water and food until the $3^{rd}$ day of the handling and habituation phase, at which point food was restricted per rat per day to 20 g Harlan Laboratory Chow (Harlan Teklad Global Rodent Diets, WI). This was determined to be in excess of the daily caloric requirement as outlined in the *Nutrient Requirements of Laboratory Animals J.*

The $1^{st}$ and $2^{nd}$ mandibular molars on the same facial side were extracted, with the side of extraction alternating between groups to control for chewing bias. Animals were anesthetized with an intraperitoneal (i.p.) injection of a 40 mg/mL ketamine hydrochloride (Mylan Industries LLC, IL, USA), 8 mg/mL xylazine (Lloyd Laboratories, IA, USA), and 0.5 mg/mL acepromazine maleate (Phoenix, MO, USA) mix. Eyes were lubricated with an ophthalmic ointment (Altaire Pharmaceuticals, Inc., NY, USA) to prevent over-drying, a heat source was provided to prevent hypothermia, and 2 mL 0.9% sodium chloride (Baxter, IL, USA) was administered subcutaneously (s.c.) as supportive therapy. Once a surgical plane of anesthesia was confirmed, 2 mg/kg bupivacaine (Hospira, IL, USA) was administered s.c. in the facial area near the extraction site [4]. Following this, the lip and tongue were gently pulled back with gloved fingers, and the gum carefully cut away from the molars with a #22 scalpel blade (Miltex, Germany). Once the roots were exposed, the teeth were loosened by being gently rocked backwards and forwards, and removed with a standard Blumenthal rongeur (World Precision Instruments, FL, USA). Blood and saliva were washed out of the mouth, the tooth socket dried as much as possible, and the hemostatic composite packed down into the socket.

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings. Consequently, while the present invention has been described with reference to particular embodiments, modifications of structure, sequence, materials and the like apparent to those skilled in the art still fall within the scope of the invention as claimed by the applicant.

What is claimed is:

1. A malleable sustained release formulation designed for packing and sticking in a dental extraction cavity, a surgical cavity or a wound cavity of a patient, the formulation comprising:
   a homogenous dry blend including
      a. a local anesthetic formulated into sustained release microparticles of a size between 0.1 and 100 microns, the microparticles encapsulating the local anesthetic for forming a primary sustained release vehicle for the local anesthetic by diffusion from the microparticles, and
      b. a gelatin powder, wherein the gelatin is selected from the group consisting of a bovine skin hemostatic agent and porcine skin hemostatic agent and having a Bloom value of about 200 to about 400; and
   an aqueous solution in an amount of about 1.5 to about 10 parts by weight to about 1 part by weight of the gelatin powder within the dry blend,
   wherein the gelatin powder and the aqueous solution form a gelled matrix with the local anesthetic sustained release microparticles incorporated into and suspended within the gelled matrix such that the gelled matrix comprises a secondary sustained release vehicle for the local anesthetic microparticles by diffusion through the matrix, and
   wherein the gelled matrix is present in an amount of about 1 to about 7 parts by weight to 1 part by weight of the local anesthetic microparticles such that the gelled matrix with the local anesthetic microparticles suspended therein is a malleable putty prior to its insertion into the cavity of a patient such that a bolus of the malleable formulation can be mixed by hand under low shear ambient conditions for molding a bolus manually sized and shaped to fit the cavity and be retained therein.

2. The formulation according to claim 1 wherein the local anesthetic is selected from the group consisting of bupivacaine, ropivacaine, dibucaine, etidocaine, tetracaine, lidocaine and xylocaine.

3. The formulation according to claim 1 which further comprises an augmenting agent.

4. The formulation according to claim 1 which further comprises an anti-infective.

5. The formulation according to claim 1 wherein poly(lactic-co-glycolic acid) is utilized to form sustained release microparticles of the anesthetic.

6. The formulation according to claim 1 wherein the anesthetic is bupivacaine.

7. The formulation according to claim 1 which further comprises thrombin.

8. The formulation according to claim 1 wherein the anesthetic begins its effect by between at least about an hour and about 5 hours when the anesthetic is utilized after any other local or topical anesthetics first.

9. The formulation according to claim 1 wherein when the formulation is not to be utilized after any other local or topical anesthetics and the onset of action of the formulation is immediate upon placement in the cavity.

10. The formulation according to claim 1 wherein the formulation further comprises an additional local anesthetic not in microparticles.

11. The formulation according to claim 1 wherein the local anesthetic begins its effect in about 1 to 5 hours.

12. The formulation according to claim 1 wherein the local anesthetic duration is up to about 5 days.

13. A malleable sustained release formulation designed for packing and sticking in a dental extraction cavity, a surgical cavity or a wound cavity of a patient, the formulation comprising:
    a homogenous dry blend including
       a. bupivacaine formulated into sustained release microparticles formed from poly(lactic-co-glycolic acid) of a size between 0.1 and 100 microns, the microparticles encapsulating the bupivacaine for forming a primary sustained release vehicle for the bupivacaine by diffusion from the microparticles, and
       b. a gelatin powder comprising a porcine skin hemostatic agent having a Bloom value of about 200 to about 400; and
    an aqueous solution in an amount of about 1.5 to about 10 parts by weight to about 1 part by weight of the gelatin powder within the dry blend,
    wherein the gelatin powder and the aqueous solution form a gelled matrix with the bupivacaine sustained release microparticles incorporated into and suspended within the gelled matrix such that the gelled matrix comprises a secondary sustained release vehicle for the bupivacaine microparticles by diffusion through the matrix, and
    wherein the gelled matrix is present in an amount of about 1 to about 7 parts by weight to 1 part by weight of the bupivacaine microparticles such that the gelled matrix with the bupivacaine microparticles suspended therein is a malleable putty prior to its insertion into the cavity of a patient such that a bolus of the malleable formulation can be mixed by hand under low shear ambient conditions for molding a bolus manually sized and shaped to fit the cavity and be retained therein.

* * * * *